United States Patent [19]

Wuchinich

[11] Patent Number: 5,167,619
[45] Date of Patent: Dec. 1, 1992

[54] APPARATUS AND METHOD FOR REMOVAL OF CEMENT FROM BONE CAVITIES

[75] Inventor: David G. Wuchinich, New York, N.Y.

[73] Assignee: Sonokineticss Group, Hoboken, N.J.

[21] Appl. No.: 529,029

[22] Filed: May 25, 1990

Related U.S. Application Data

[63] Continuation-in-part of Ser. No. 439,114, Nov. 17, 1989.

[51] Int. Cl.$^5$ .............................................. A61B 17/56
[52] U.S. Cl. ...................................... 604/22; 604/28; 604/35; 604/43; 128/24 AA; 606/99; 606/169; 606/171
[58] Field of Search ................ 606/46, 128, 169, 170, 606/174, 53, 79, 84, 86, 88, 99, 171; 604/22, 28, 27, 43, 35; 128/24 AA

[56] References Cited

U.S. PATENT DOCUMENTS

| | | | |
|---|---|---|---|
| 2,742,076 | 4/1956 | Klein | 29/427 |
| 3,401,446 | 9/1968 | Obeda et al. | 156/344 X |
| 3,526,219 | 9/1970 | Balamuth | 128/2 |
| 3,589,363 | 6/1971 | Banko et al. | 128/276 |
| 3,614,484 | 10/1971 | Shoh | 310/8.2 |
| 3,683,736 | 8/1972 | Loose | 264/25 X |
| 3,809,977 | 5/1974 | Balamuth | 318/116 |
| 4,203,444 | 5/1980 | Bonnell et al. | 128/276 |
| 4,223,676 | 9/1980 | Wuchinich et al. | 128/276 |
| 4,248,232 | 2/1981 | Engelbrecht et al. | 128/24 AA |
| 4,428,748 | 1/1984 | Peyman et al. | 604/22 |
| 4,493,694 | 1/1985 | Wuchinich | 604/22 |
| 4,504,264 | 3/1985 | Kelman | 604/22 |
| 4,603,694 | 8/1986 | Wheeler | 604/22 |
| 4,643,717 | 2/1987 | Cook et al. | 604/22 |
| 4,702,236 | 10/1987 | Tarabichy et al. | 128/92 V |
| 4,750,488 | 6/1988 | Wuchinich et al. | 128/303 R |
| 4,750,902 | 6/1988 | Wuchinich et al. | 604/22 |
| 4,828,052 | 5/1989 | Duran et al. | 175/55 |
| 4,838,853 | 6/1989 | Parisi | 604/22 |
| 4,846,161 | 7/1989 | Roger | 128/92 V |
| 4,873,969 | 10/1989 | Huebsch | 128/92 R |
| 5,019,083 | 5/1991 | Klapper et al. | 606/99 |

FOREIGN PATENT DOCUMENTS

| | | |
|---|---|---|
| 121491 | 10/1984 | European Pat. Off. . |
| 243298 | 10/1987 | European Pat. Off. . |
| 2614524 | 11/1988 | France . |
| 203299 | 10/1983 | German Democratic Rep. . |
| 1371335 | 10/1974 | United Kingdom . |

OTHER PUBLICATIONS

Krawitt et al., Ultrasonic Aspiration of Prostate, Bladder Tumors and Stones, *Urology*, 30:6 (1987) pp. 578–580.

Richmond et al., Evaluation of the Histopathology of Brain Tumor Tissue Obtained by Ultrasonic Aspiration, *Neurosugery*, 13:4 (1983), pp.415–419.

Malloy et al., Transurethral Ultrasonic Aspiration of the Prostrate, A.U.A., May 1989.

Epstein et al., Surgical Management of Extensive Intramedullary Spinal Cord Astrocytoma in Children, Concepts in Pediatric Neurosurgery, 2, (1982) pp. 29–44.

Sternlieb et al., Ultrasonic Restoration of Severlky Calcified Aortic Valve, *The Lancet*, Aug. 20, 1988, p.446.

Caspari, Current Development of Instrumentation for Arthroscopy, *Clinics in Sports Medicine*, 6:3 (1987), pp. 626–627.

Johnson, Arthroscopic Surgery:Principles and Practice (3rd Edition), Verlag Springer (1986), pp. 244–245.

Brochure, Endo–Urology—A Breakthrough in Ultrasonic Lithotripsy, Karl Storz Endoscopy—America, Inc. (1984).

Brochure, Instruments and Apparatus for Lithotripsy, Richard Wolf GMBH, Knittlinger, West Germany (1984).

Brochure, Percutaneous Low Pressure Universal Nephroscope, Richard Wolf, Knittlinger, West Germany, (1984).

Brochure, *Sonic Surgery System*, Quintron, Inc.

Klapper and Caillouette, "The Use of Ultrasonic Tools in Revision Arthoplasty Procedures", *Contemporary Orthopaedics*, vol. 20, No. 3, pp.273–279, (Mar. 1990).

Goliamina, "Ultrasonic Surgery", *Proceedings of the Eighth International Congress on Acoustics*, London, pp.63–69, (1974).

Ensminger, "Ultrasonics: Fundamentals, Technology, Applications", *Marcel Dekker Inc.*, pp. 462–467 (1988).

X. Zhou, et al., Effect of Press-Fit Femoral Stems on Strains in the Femur, 5 J. Arthroplasty 71 (1990).

J. Schwartz, Jr., et al., Femoral Fracture During Non-Cemented total Hip Arthroplasty, 71-A J. Bone & Joint Surgery 1135 (1989).

H. Cameron, Proximal Femoral Ostectomy in Difficult Revision Hip Surgery: How to Revise the Unrevisable, 18 Contemp. Orthopaedics 565 (1989).

R. Karpman, et al., The Lithotriptor and Its Potential Use in the Revision of total Hip Arthroplasty, 16 Orthopaedic Rev. 81 (1987).

J. Moreland, et al., The Window Technique for the Removal of Broken Femoral Stems in Total Hip Replacement, 212 Clinical Orthopaedics and Related Research 245 (1986).

S. McClelland, et al., Atraumatic Removal of a Well-Fixed Porous Ingrowth Hip Prosthesis, 15 Orthopaedic Rev. 75 (1986).

P. Lin, Posterior Interbody Fusion Technique: Complications and Pitfalls, 193 Clinical Orthopaedics and Related Research 90 (1985).

W. Harris, et al., A New Technique for Removal of Broken Femoral Stems in Total Hip Replacement, 63-A J. Bone & Joint Surgery 843 (1981).

Richards Mfg. Co., Orthopedic Catalog (1981).

E. Weis, Jr., A Sonic Tool for Spinal Fusion, 8 Orthopedic Clinics of North Am. 43 (1977).

De Puy Inc., Catalog (1966).

*Primary Examiner*—William E. Kamm
*Assistant Examiner*—Kevin Pontius
*Attorney, Agent, or Firm*—Robert M. Skolnik

[57] ABSTRACT

A surgical apparatus having a handpiece, a vibration source with the handpiece for generating mechanical vibrations in response to current supplied thereto, and elongated hollow tool operatively associated with the vibration source and attached to the handpiece at a point where essentially no vibrational motion occurs, the tool extending away from the handpiece to the cement to be removed. A method removing cement using the surgical apparatus by applying the tool to the cement and thereby applying mechanical vibration to the cement causing the cement to melt. Removing the cement by suction through the hollow elongated tool. Additional alternate method steps include rotating the tool to apply shear forces to the cement being removed, cooling and damping lateral vibrations at the tool end, and irrigating the cement while melting and removing it. Associated with the alternate method steps are embodiments of the apparatus including a motor for rotating the elongated tool while vibrating and a concentric tubular members for cooling, damping, irrigation and aspiration.

33 Claims, 4 Drawing Sheets

APPARATUS AND METHOD FOR REMOVAL OF CEMENT FROM BONE CAVITIES

CROSS REFERENCE TO RELATED APPLICATIONS

This present application is a continuation-in-part of application Ser. No. 07/439,114, filed Nov. 17, 1989.

BACKGROUND OF THE INVENTION

The present invention relates to surgical instruments and procedures; in particular to rotary and nonrotary aspirators capable of removing bone cement from bone canals in the replacement and repair of prosthetic bone implants and to a method for removing bone cement in such procedures.

The use of ultrasonic vibration to enhance the performance of surgical mechanical cutting and forming implements such as saws, knives, and spatulas is generally known in the art (Goliamina, *Ultrasonic Surgery*, Proceedings of the Eighth Int'l. Cong. on Acoustics, London, 1974 pp. 63-69). East German Patent No. 203,229 discloses an ultrasonically activated knife for general surgical application which is intended to increase both the precision and quality of incisions. The application of mechanical vibration to cutting and parting tools is therefore not new to surgical practice and has, in fact, resulted in the commercial introduction of at least one ultrasonically powered instrument for use in cutting cancellous and cortical bone.

The development of prosthetic joints for the hip, knee, elbow and shoulder has offered another application for ultrasonically vibrating instrumentation. Typically, these artificial joints are cemented into a surgically created cavity in the bone. In the case of the hip, the head and neck of the femur are removed, a cavity is reamed into the shaft and the stem of the implant is cemented into this cavity. The cement used is typically methylmethacrylate, an acrylic thermoplastic. These man made joints have an average life of about 10 years, after which they must be replaced. Usually after this time, either the implant itself loosens in the cement, or the cement becomes partially separated from the bone.

Repair of a prosthetic joint requires that first the implant be removed and then all cement be excavated from the cavity. In most cases, the implant is loose upon presentation. The cement, however, is usually found rigidly adherent to the bone. A number of powered rotary burrs have been developed to assist the surgeon in thoroughly cleaning this cavity. These burrs are effective in abrading the plastic, but, because the plastic bone cement is much harder than the surrounding cortical bone, their proper use requires extensive practice in manipulation. Often the cavity is as much as 10 inches deep. Guiding a high speed rotary burr tip at this distance while avoiding inadvertent contact with bone is very difficult to achieve.

Frequently, the surgeon will resort to fluoroscopy as an aid in ensuring that all the residual cement (which contains radio-opaque material) has been removed. Even under the best of circumstances, however, some damage to adjacent bone is inevitable. Melon-ball bone pockets produced by the soft-seeking burr are a constant concern to the orthopedic surgeon because they weaken the cavity into which a new implant must be introduced.

Of all rotational skeletal attachments, the hip joint, in particular, bears the greatest portion of the human body weight. Inasmuch as the implant procedure itself weakens the femur by creating a cavity in otherwise solid supporting physiological matter, any additional enlargement of the original opening presents a risk of future failure, principally through perforation of the bone itself by the implant when subject to the imposed stress of therapeutic exercise or accident. Quite naturally, no surgeon welcomes a repair that, however expertly performed originally, suffers the limitations of his tools. Because access is restricted, the cement is usually firmly adherent and preservation of the remaining structural integrity of the femur is paramount. Hip revision, as this procedure is known, can require as much as 3 or 4 hours to successfully complete. Much of this time is spent in meticulously removing cement.

Recent advances in the art include ultrasonically vibrating spatulas and styluses to separate the plastic cement from the implant and the bone (Klapper and Caillouette, *The Use of Ultrasonic Tools in Revision Arthoplasty Procedures*, 20: 3 Contemporary Orthopaedics, pp. 273-279) (March 1990). These advances exploit the inability of plastics, and particularly thermoplastics, to suffer cyclic deformation well. Metals and some ceramics have a crystalline or amorphous molecular structure that does not impede the transmission of sound waves. In plastics, however, sound transmission is always accompanied by the generation of heat. If exposed to sound pressures readily conveyed by metallic structures, such as those employed by ultrasonic dental tools and surgical aspirators, virtually all plastics will rapidly heat, melt and even vaporize.

This susceptibility of thermoplastics to intense vibration occurring at an ultrasonic frequency, is the basis of ultrasonic plastic welding—a process widely used in industry to join molded plastic parts for a variety of uses ranging from toys to household appliances (e.g., Ensminger, *Ultrasonics: fundamentals, technology, applications*, pp. 462–467 (1988 Marcel Dekker Inc.)). Usually, in this process, two mating halves of a plastic part are placed in contact within a nest that conforms to the surface of one of two parts to be joined. An ultrasonic horn, whose face conforms to the exposed surface of the other part, is then brought into intimate contact, under applied pressure, with the assembly. Vibration of the horn is transmitted to the parts. Although the entire plastic is subject to the vibration, the joint between the halves is structurally much weaker than the otherwise homogeneous portions and softens and melts well before any deformation occurs elsewhere. Once the joint melt occurs, vibration ceases, the melt recrystallizes and the bonded part is removed from the nest. Even the strongest reinforced thermoplastics can be joined in this manner within a few seconds.

Direct application of a vibrating tool will also produce local melting (Klapper and Caillouette, supra). By controlling both the contact pressure and the amplitude of vibration, softening can be modulated so that the cement can be transformed into a putty and gently released either from the implant stem or cortical bone. Because the bone is not plastic, and is, in fact, with the exception of tooth enamel, the best anatomical conductor of sound in the human body, it is not deformed by contact with the stylus. Ultrasonic vibration therefore reverses the effect encountered in the use of rotating burrs. The ultrasonic tip moves into the plastic far more easily than into the bone. Ultrasonic excavation is therefore much more easily controlled, even over a distance of 10 to 12 inches, and risk of inadvertent bone damage is significantly reduced when compared to the performance of instruments such as burrs which abrade rather than melt material.

The transformation of phase produced by vibration, although caused by the heat generated from the large cyclic strain losses in plastic, is far more localized than that produced, for example, by a heated tip such as is described in U.S. Pat. No. 4,873,969 to Huebsch. Because the sound waves rapidly propagate in an approximately spherical pattern, the cyclic stress levels rapidly diminish beyond the point of contact. Consequently, only material with a few millimeters of tip contact is softened or melted. On the other hand, a directly heated tip encounters a thermal sink in the cement which draws the energy into the entire surrounding structure. This situation dictates that inordinate amounts of energy have to applied to obtain local melting. In the process thermal elevation of bone as well as the cement occurs. When working close to the bone, a condition that prevails in the lower one third of the cavity, the temperatures so produced can cause tissue necrosis.

The temperature at the operating tip of an ultrasonic aspirator can be controlled to a degree by a preaspiration device. Such a device is disclosed in U.S. Pat. No. 4,493,694 to Wuchinich and includes a sleeve around a central vibrating aspiration tube and holes in the aspiration tube communicating with the passage defined by the sleeve. Irrigating fluid is supplied through the sleeve to cool the tip and is sucked into the aspirating tube through the small holes.

SUMMARY OF THE INVENTION

It is therefore an object of the invention to provide a method for removing cement from bone cavities which reduces the possibility of damage to the bone itself. As such, a feature of the invention is to utilize mechanical vibration to breakdown and melt the cement. A further feature is a surgical apparatus capable of applying mechanical vibration to the cement without damaging the surrounding bone if contact is made. These features have the advantage of reducing the degree of precision required by the surgeon and thereby increasing the speed and effectiveness of the procedure.

A further object of the invention is to provide a means for aspirating cement in bone cavities with an easily manipulated surgical apparatus while simultaneously cooling and damping lateral vibrations in the apparatus. Therefore a feature of the invention is concentric means for cooling and aspiration. This allows cooling fluid to be directed precisely to the point where cooling is required, while minimizing the size of the apparatus and tool in contact with the cement. Additionally, cooling fluid may be used for irrigation if desired.

Another object of the invention is to apply shear forces to the cement being removed in order to increase the effectiveness of the removal. A feature of the invention is therefore a rotating tool with a tip shaped to shear away the cement. In this manner the rate of removal of cement may be increased without increasing the possibility of damage to the surrounding bone.

These and other objects are accomplished according to the present invention by a method of removing cement from bone cavities comprising the steps of applying an end of a elongated hollow tool, capable of mechanical vibration, to the bone cement; melting an area of cement by vibration of the tool; and aspirating the melted cement by suction applied through the tool. For certain applications, additional method steps include applying shearing forces to the cement, rotating the hollow tool in contact with the cement to apply the shearing forces, cooling and damping lateral vibration in the hollow tool and irrigating the area of melted cement.

A surgical apparatus according to the invention includes a handpiece having first and second ends with a first opening defined by the first end; an elongated hollow tool extending from the first opening for contacting the cement in a bone cavity; a vibration source within the handpiece for generating mechanical vibrations in response to electrical current applied thereto, and aspiration means for withdrawing melted cement from the bone cavity. The vibration source is operatively associated with the elongated hollow tool and the tool is attached to the handpiece at a point where no vibration occurs.

The vibration source according to the invention includes a tubular piezoelectric crystal having a means for electrical contact, a union for connecting the crystal to the elongated hollow tool and a stem extending opposite from said elongated hollow tool. In a preferred embodiment of the apparatus the stem has a length which is not resonant at the operating frequency of the crystal, and the elongated hollow tool has a length of $\Gamma/4 + n\Gamma/2$ where n is 0 or an integer and $\Gamma = c/f$ where f is the frequency of operation, $\Gamma$(gamma) is a wavelength corresponding to f and c is the velocity of extensional waves in the elongated hollow tool.

In one alternate embodiment of the apparatus according to the invention a rotation means is operatively associated with the vibration source for rotating the elongated hollow tool about its longitudinal axis through at least one revolution, said rotating means enabling the elongated hollow tool to apply shear forces to the cement. The tool may be provided with a reduced opening at the end for contacting the cement and further may be cut to form a semicircular trough having longitudinally running edges for shearing the cement.

Another alternate embodiment of the surgical apparatus includes means for cooling the elongated hollow tool. In a preferred embodiment the cooling means comprises a hollow sleeve surrounding the elongated hollow tool defining an interspace between the tool and sleeve, and a hollow tube disposed inside the stem defining a second interspace between the tube and stem. The sleeve communicates with the first opening in the hand piece. While the tube communicates with the central passage in the union member for the passage of aspirated material therethrough. The second interspace communicates with the first interspace through cooling ports defined by the union member for the passage of cooling fluid therethrough. At the working end of the hollow tool the interspace communicates with the interior of the hollow tool at a point inside the end of the sleeve.

BRIEF DESCRIPTION OF THE DRAWING

The features and advantages of the invention will be more readily apparent from the following detailed description of the invention illustrated in the drawing figures, wherein.

DETAILED DESCRIPTION OF THE INVENTION

While ultrasonic vibration is eminently suited for liquifying bone cement, the object of its application is the removal of the cement from the bone cavity. Application of vibration alone can convert the otherwise rigid plastic to a flowable material, but to fully exploit the phenomena, a method of transporting the liquid cement from the bone to a repository must be introduced.

Figure 1:
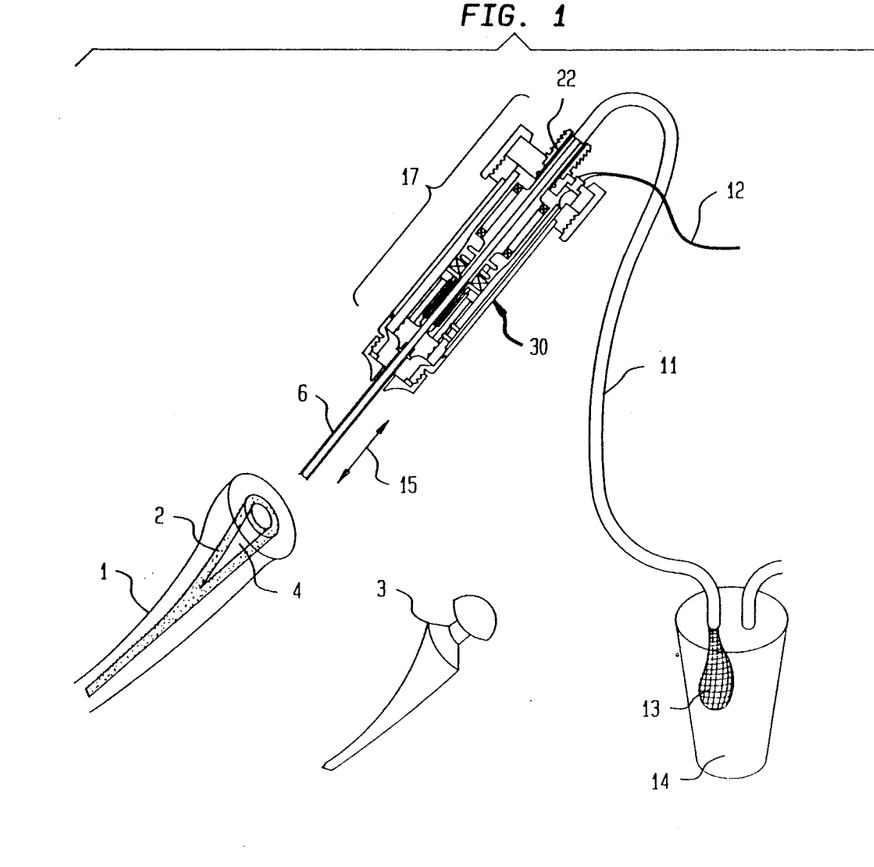
FIG. 1 is a schematic illustration of one embodiment of the apparatus and method according to the present invention, with the apparatus illustrated in cross-section.
Figure 2:
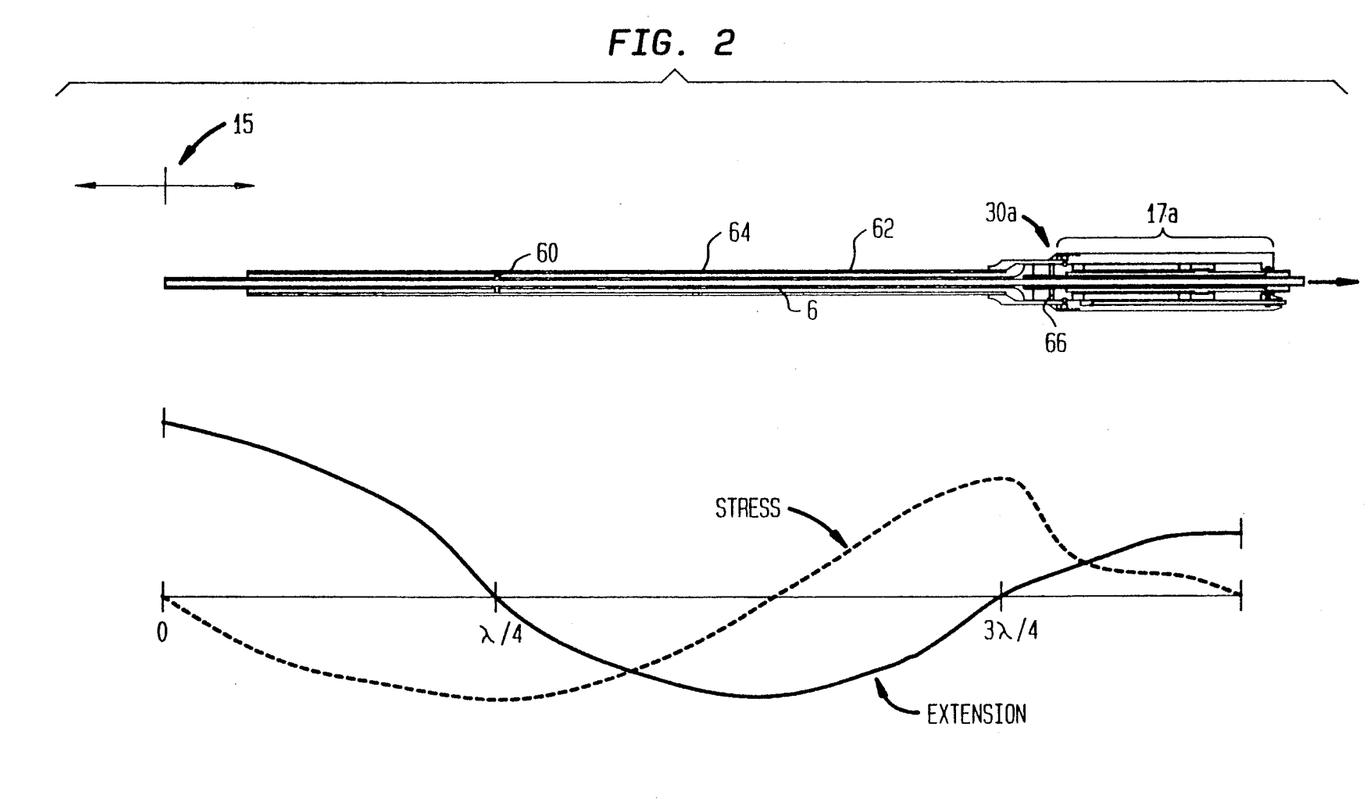
FIG. 2 is a cross-sectional view of an alternate embodiment of the apparatus of the invention.
Figure 3:
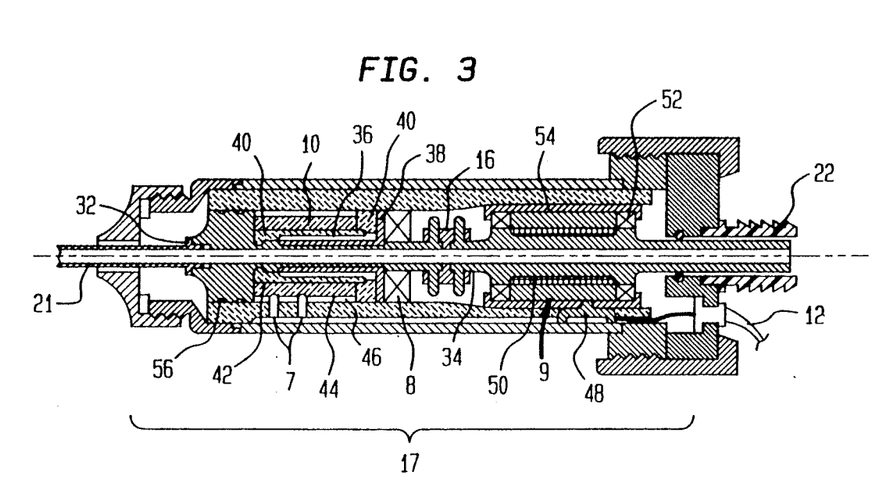
FIG. 3 is an enlarged cross-sectional view of a portion of the apparatus shown in FIG. 1.

Referring to FIG. 1, the general apparatus and method according to the invention is described below. Femor 1 is shown following removal of the prosthetic implant 3. A cavity 4 remains whose walls are lined with cement 2. This cement is excavated by the apparatus 30 having a hollow ultrasonic tip 6 that vibrates in the direction indicated by arrow 15. The tip 6 is an elongated hollow tool which is attached to handpiece 17. The apparatus 30 illustrated in FIG. 1 is one embodiment of the invention. The handpiece 17 corresponding to this embodiment is shown in detail in FIG. 3. An alternate embodiment of the apparatus according to the invention is shown in FIG. 2 and is designated 30a. The handpiece 17a corresponding to apparatus 30a is shown in FIG. 3. It will be readily appreciated by those skilled in the art that apparatus 30 in FIG. 1 may be replaced by apparatus 30a with little modification to the remaining parts. The required modification will, however, be discussed below.

Of particular interest is the form of ultrasonic motion along the transducer and tip. FIG. 2 shows both extension (peak vibration amplitude) and accompanying stress (force per unit area) within the component part of the transducer and tip 6. The direction of vibration relative to the assembly is indicated by arrow 15. Note that the stem 34, which extends from the union 32 at a point of diminished vibration, does not vibrate. The assembly of the transducer and tip are resonant as an entity at the design frequency of vibration. At points along their structure where there is little or no vibration, called the "nodes" of motion, mounting to a rigid structure such as a housing may be accomplished without impeding vibration. The magnitude of ultrasonic vibrational velocity is extremely significant. For example, a 0.001 inch peak to peak excursion at a frequency of 20 kHz has a root mean square velocity of 44 inches per second or 2.5 miles per hour. It is therefore important, if wear and the production of heat are to be minimized, that parts of the transducer in contact with stationary structures exhibit very low levels of motion. The stem, being of a length that is not resonant at the operating frequency is one such location. The O-rings on the union are another example. The raised portion of tip 50 is another node where support of the sleeve 62 can also be obtained. Note that the tip may not contact the sleeve at any point other than modal sleeve support 60 to prevent the inordinate production of heat.

The length and connection of the stem to the transducer is an important aspect of the design. Because the stem is not resonant in and of itself at the chosen operating frequency, and because it is attached to the transducer at a point of vanishing ultrasonic displacement, it has no effect upon the vibrational characteristics of the transducer and tip. Furthermore, by the same reasons, the entire stem is stationary, making connection to the motor shaft possible, if desired. If, in fact, the stem length were $\Gamma/4$, where $\Gamma$ is the wavelength of extensional waves, or was, whatever its length, attached at a point on the transducer exhibiting significant ultrasonic motion, vibration would exist at the motor shaft connection, satisfactory operation could not be sustained. The motor bearing, windings and insulation would be rapidly degraded under vibration at ultrasonic frequencies. The absence of vibration on the stem also permits use of a conventional support bearing 5 for the transducer.

Although the tip is ¾ of a wavelength, $\Gamma$, long, it may be of any length that satisfies the boundary conditions: i.e., (1) vanishing motion at its point of attachment to the transducer union and (2) vanishing stress at its open end. Solution of the wave equation for a uniform prismatic tube, subject to these conditions, dictates that the tip length, L, be such that $$L = \Gamma/4 + n\Gamma/2 \tag{1}$$

wherein n is an integer (0,1,2...) and $\Gamma = f/c$ where f is the frequency and c is the velocity of extensional waves in the tip.

The releasable tip is shown attached at a quarter wavelength point on the transducer so as to take advantage of the large difference in cross-sectional areas between the transducer and tip to produce an increase in vibrational amplitude. It can be shown, for such a structure, that this increase or gain G, can be expressed as $$G = (\sigma_e c_e S_e)/((\sigma_t c_t S_t) \tag{2}$$

where $\sigma$ is the density, c is the sound velocity and S is the cross sectional area. The subscript e and t refer to the effective values for the transducer and tip respectively. If this reduction in cross sectional area is not made, the motion produced by the transducer will not be sufficient to dissect tissue. Typically, piezoelectric transducers can produce about 0.001 inch peak to peak displacement at a frequency of 20 kHz. With the reduction at the $\Gamma/4$ point, the tip end displacement can easily attain 0.001 to 0.020 inch, peak to peak.

The apparatus according to the present invention is generally constructed in accordance with the principles of U.S. patent application Ser. No. 07/439,114, filed Nov. 17, 1989, the content of which is expressly incorporated herein by reference thereto.

Figure 4:
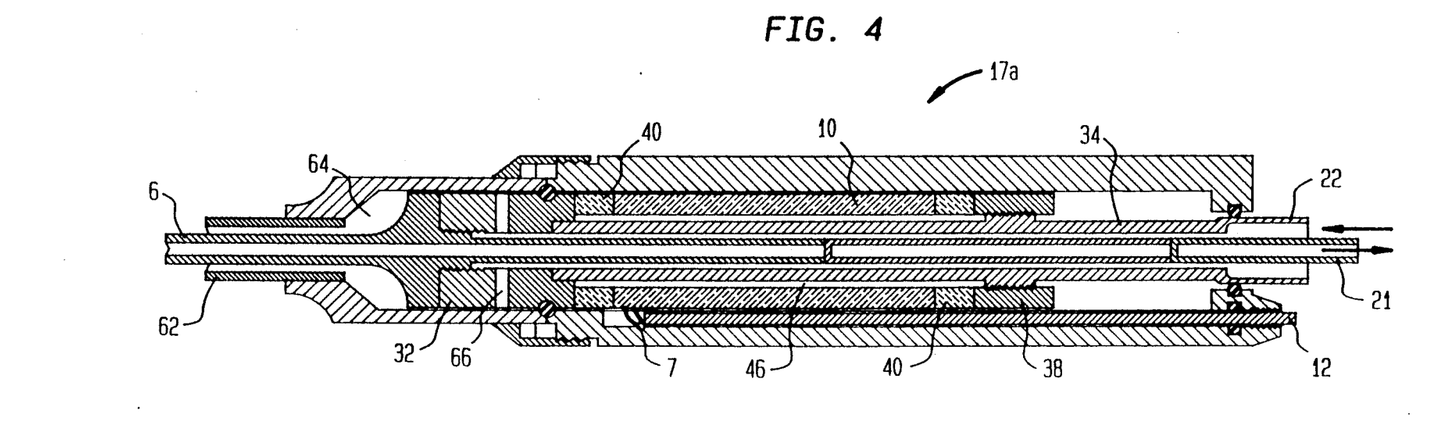
FIG. 4 is an enlarged cross-sectional view of a portion of the apparatus shown in FIG. 2.

FIG. 3 shows the ultrasonic and rotational components of the apparatus. FIG. 4 shows an embodiment of the invention which does not utilize the rotational aspects of the invention, however, like numerals refer to like parts in both FIGS. 3 and 4. The ultrasonic transducer assembly includes a union 32 where the surgical tip 6 is attached. This union is integral with a stem 34 which enters a motor coupling 16. The free end of the stem 34 terminates in a fitting 22 permitting the attachment of tubing 11. In both apparatus 30 and 30a the fitting does not rotate. A spindle 36 is attached to the union 32 by threads and, with the use of the prestress nut 38, holds the assembly together under the extension and contraction of vibration. Optional ceramic insulator rings 40 are sandwiched on each side of the tubular piezoelectric crystal 10.

The crystal 10, typically made of polycrystalline zirconium titanate, contains electrodes covering its inner 42 and outer 44 surfaces, with the inner electrode wrapped around the left edge and onto the outer diameter. An electrical insulation air gap 46 separates the inner electrode from the spindle 36. In FIG. 3, brushes 7 are held in contact with these electrodes by springs. Because the embodiment shown in FIG. 4 does not rotate, the electrical connections 7 are direct to the crystal 10, without the need for electrodes 42 and 44. In crystals of the type shown, a voltage applied between the electrodes produces a change in the axial length of the tube, thereby supplying the means for exciting vibration.

The stem 34 does not vibrate so that it can be attached to an electric motor 9 as shown in FIG. 3 through an insulated motor coupling 16. The motor 9 may be any one of a number of types such as a stator winding 48 and an armature 50 which rotates. Bearings 52 support the rotation of the armature within the motor housing 54. The transducer is driven in rotation by the motor 9 through the coupling 16 and is itself supported on a bearing 8 and O-ring seals 56. The embodiment shown in FIG. 4, of course, does not employ a motor because rotation is not required.

The insulating materials employed should have dielectric properties approaching that of a vacuum. The material for insulator ring 40 should also have acoustic properties approaching or exceeding those of the piezoelectric material 10, since these rings are exposed to large cyclic stress at the frequency of vibration. For example, nylon may be used for the insulating material 16 of the coupling which is not subject to vibration, but a ceramic such as MACOR (Trademark of Corning Glass Works, Corning, N.Y.), which exhibits both a dielectric constant only several times that of free space and elastic losses typical of metals, is preferably used for the insulator rings 40. Exposed to the magnitude of cyclic stress generated by the transducer (i.e., about 3,000 pounds per square inch) at a frequency of 10-50 kHz, virtually all common plastics will melt or decompose.

Insulation of the piezoelectric crystal 10 from all other electrically conductive components also isolates the ultrasonic generator supply from the surgical tip 6, thereby ensuring that no unintentional currents flow through the subject. Although it is possible to isolate the ultrasonic generator from its supply of operating room utility current, the insulator rings 40 preferably afford additional and usually the desired level of protection.

Referring again to FIG. 1, the tubing 11 is connected to a vacuum canister 14 which serves as a receptacle. This canister is connected to a source of suction. The suction source may be provided by standard wall connection to a central operating room vacuum system or to a separate, regulated, suction pump. An optional trap 13 may be used to collect solid matter passing through the tubing.

As discussed previously, the alternative embodiment of the apparatus 30a shown in FIGS. 2 and 4 does not employ rotation of the tip 6. The apparatus 30a as shown is, however, designed for concentric cooling, damping of lateral vibration and aspiration. Cooling and damping are optional in application and it will also be readily apparent to those of ordinary skill in the art that the feature of concentric cooling, damping and aspiration could be equally applied to the embodiment of the apparatus 30 employing a rotating tip.

As can be seen best in FIG. 4, aspiration occurs through the tip 6 which is formed with the union 32. An aspiration tube 21, inside stem 34 communicates with the tip 6 through union 32. Cooling and damping flow is admitted to an interspace 64 between a sleeve 62 and the tip 6 by ports 66 drilled at right angles through the end of the transducer coupled to the tip 6. The sleeve 62 is supported by the nodal sleeve support 60 at a point where no vibration of the tip occurs. A flexible tube similar to tube 11 shown in FIG. 1, but allowing for both aspiration and cooling and damping flow in a concentric arrangement as indicated in FIG. 4, is attached to fitting 22.

In addition to cooling the tip 6 the cooling flow is employed to damp excessive vibration at the end 5 of tip 6. Cooling and damping may be achieved with the tip end 5a, shown in FIG. 6. Trough 19a extends back and into the opening defined by sleeve 62. This allows a free flow of cooling fluid from interspace 64 into the tip 6 without contacting end 5a and obscuring the surgeon's vision of the work area. In addition to cooling the tip 6, the tip end construction shown in FIG. 6 performs an important function in minimizing lateral vibration of the tip end 5. The fluid in interspace 64 surrounds the tip at the end and thus acts as a buffer against lateral vibration.

Figure 6:
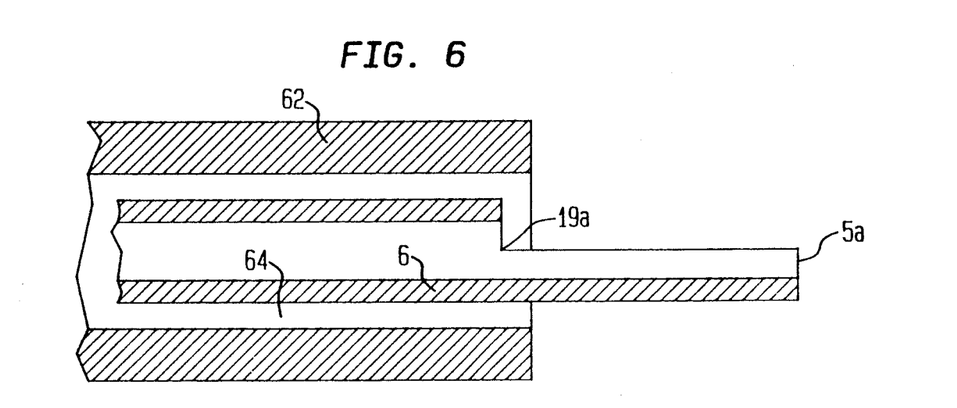
FIG. 6 is a section view of a tip end embodiment for cooling and damping lateral vibrations of the tip end.

The location of the back of trough 19a may be varied to control the amount of cooling fluid entering the tip 6 at that point. In this manner, and by controlling the overall flow of the fluid, the cooling fluid may be also utilized for irrigation if desired.

Figure 5A:
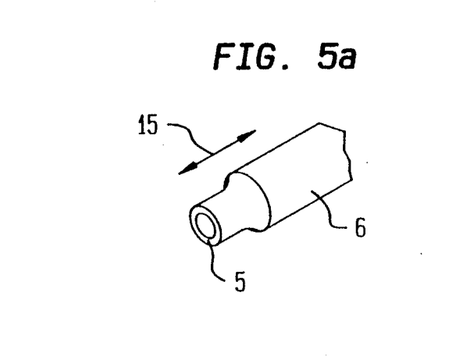
FIGS. 5a and 5b are perspective views of two possible end embodiments for the apparatus of FIG. 1.

In operation the handpiece is connected by cable 12 to a source of ultrasonic frequency electrical current to power the transducer and in apparatus 30, and run the motor 9. The vibrating tip is then applied to the rim of cement 2. The application locally melts the cement material 2 which is then drawn into the tip 6 by the applied suction. Within the tip 6, the cement recrystallizes into a solid sliver which is then deposited in the vacuum canister 14. Because the cement 2 rapidly reforms into a solid, the end 5 of the ultrasonic tip 6 has a reduced opening as shown in FIG. 5a. This reduction prevents cement from lodging within the tip 6 since it is excavated by an annulus having a smaller diameter than the ensuing conduit.

Figure 5B:
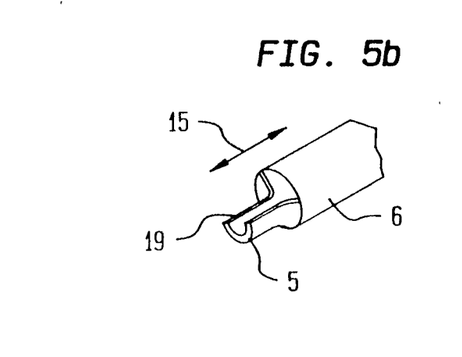

In the rotating embodiment, apparatus 30, the end 5 may also be semicircular 19 in cross section as shown in FIG. 5b. Since the tip may be rotated by the motor, such a modification nevertheless results in effective liquefaction and aspiration. However such a tip possessing, as it does, edges parallel to the axis of the tip, exposes the cement to shearing as well as extensional vibration. In some instances, this shearing or cutting action is extremely effective in rapidly dissecting the cement.

The preferred range of ultrasonic frequencies employed by this invention is from 10 to 50 kHz. The magnitude of tip vibration suitable for cement removal extend from 0.001 to 0.020 inches peak to peak. The tip 6 may be a one quarter wavelength long or one quarter plus a integral multiple of one half wavelength long. For example, if the tip 6 is titanium and the frequency of operation is 20 kHz, the tip may be 2.5, 7.5, 12.5, etc.

inches in length. The opening at tip end 5, through which the melted cement passes, may be as small as 0.062 inch or as large as one half inch.

As is apparent from the alternate embodiments, arthroplasty using this invention does not necessarily require the use of rotation. Even with apparatus 30 the motor may be deactivated while the ultrasonic transducer is energized. In some instances, however, rotation will result in more rapid and effective removal of the cement, particularly in those regions near the bone. In these situations, the semicircular tip may be employed to assure complete exposure of all edges, both those producing vibrational shear and those producing extension, to the cement over a complete revolution of 360 degrees. When rotation is used, the preferred rate lies between 0.001 and 10,000 rpm.

Also as discussed above, the tip length of apparatus 30a may be any odd multiple of a quarter wavelength. Therefore, if the frequency of operation is 20 kHz and if the tip is made of titanium, the tip may be 2.5, 7.5, 12.5, etc. inches long. The range of tip vibrational movement is 0.001 to 0.02 inches peak to peak, at 20 kHz.

What is claimed is:

1. A method of unidirectionally removing cement from bone or bone cavities containing same which comprises:
   applying mechanical vibrations to cement adherent on a bone or bone cavity of a subject to melt an area of the cement by vibration; and
   removing the melted cement unidirectionally from the bone or bone cavity by suction or aspiration wherein no traumatic force is applied to said bone.

2. The method of claim 1 which further comprises shearing the cement from the bone or bone cavity.

3. The method of claim 2 wherein the cement is sheared while the mechanical vibrations are applied to the cement present in the bone or bone cavity.

4. The method of claim 1 which further comprises collecting the melted cement after removal from the subject.

5. The method of claim 1 which further comprises irrigating the cement and bone or bone cavity to assist in the removal of the cement.

6. The method of claim 1 wherein ultrasonic mechanical vibrations are applied to the cement essentially simultaneous with a suction or aspiration for removal of melted cement.

7. A method of unidirectionally removing cement from bone cavities, comprising:
   applying an end of an elongated hollow tool, capable of mechanical vibration, to the bone cement;
   melting an area of cement by vibration of the hollow tool; and
   aspirating the melted cement by suction applied through said hollow tool,
   wherein the melted cement is unidirectionally removed through said hollow tool.

8. The method of claim 7, wherein the elongated hollow tool applied to the cement is a part of a surgical apparatus, said apparatus further comprising:
   a handpiece having first and second ends with a first opening defined by the first end and said tool extending from said first opening;
   a vibration source within the handpiece for generating mechanical vibrations in response to electrical current applied thereto, said vibration source operatively associated with the elongated hollow tool with said tool being attached to the handpiece at a point where no vibration occurs; and
   aspiration means for withdrawing melted cement from the bone cavity, so that the method includes controlling the application of the vibrations.

9. The method of claim 8, further comprising rotating said tool to apply shearing forces to the bone cement.

10. The method of claim 9, wherein the apparatus further comprises rotation means operatively associated with said vibration source for rotating the elongated hollow tool enabling said tool to apply shear forces to said cement and wherein said elongated hollow tool is rotated about its longitudinal axis through at least one revolution.

11. The method of claim 10, which further comprises selecting the opening of the elongated hollow tool at the end applied to the cement to have a reduced diameter portion relative to the rest of said tool to focus the mechanical vibrations upon the area of cement to be melted.

12. The method of claim 11, wherein the reduced diameter portion of the elongated hollow tool forms a semicircular trough having longitudinally running edges and said edges are applied to said cement for increased shearing of the melted cement while the tool is rotated.

13. The method of claim 10, which further comprises generating rotational forces by a motor and transmitting said forces to said vibration source and to said elongated hollow tool for rotation thereof.

14. The method of claim 8, which further comprises cooling the elongated hollow tool and damping lateral vibrations at the end of said hollow tool.

15. The method of claim 14, which further comprises irrigating the area of melted cement to assist in removal of the melted cement.

16. The method of claim 14, which further comprises orienting and positioning means for cooling and dampening the hollow tool, concentrically with the aspiration means to assist in the removal of the melted cement.

17. A method of unidirectionally removing cement from a bone or bone cavity, which comprises:
   placing a surgical apparatus, including a handpiece, a vibration source within the handpiece for generating mechanical vibrations in response to electrical current applied thereto, an elongated hollow tool operatively associated with said vibration source and attached to said handpiece at a point where essentially no vibration occurs, means for aspiration of the cement, and means for cooling and damping said hollow tool, in contact with the cement at an end of the elongated hollow tool;
   melting the cement by applying energy to said vibration source and thereby transferring mechanical vibration to the cement through the elongated hollow tool to melt said cement without apply traumatic force to the bone;
   aspirating the melted cement by applying suction to remove said cement unidirectionally through said elongated hollow tool; and
   selectively cooling and damping lateral vibrations in said hollow tool as required to aid in aspirating by applying a cooling fluid to said elongated hollow tool.

18. The method of claim 17, which further comprises irrigating the area of melted cement to assist in removal of the melted cement.

19. The method of claim 17 which further comprises shearing the melted cement from the bone or bone cavity.

20. The method of claim 19, wherein the melted cement is sheared by rotating the hollow tool.

21. A surgical apparatus for removing cement from bone or bone cavities comprising:
   an elongated hollow tool for applying mechanical vibrations to cement present on a bone or bone cavity of a subject to melt the cement by vibration;
   means for removing the melted cement from the bone or bone cavity unidirectionally through the elongated tool by suction or aspiration;
   a handpiece having first and second ends with a first opening defined by the first end and said tool extending from said first opening;
   a vibration source within the handpiece for generating mechanical vibrations in response to electrical current applied thereto, said vibration source operatively associated with the elongated hollow tool to vibrate said tool with said tool being attached to the handpiece at a point where no vibration occurs; and
   means for rotation of said tool operatively associated with said vibration source wherein said means for rotation enables said tool to rotate about its longitudinal axis through at least one revolution while vibrating to apply shearing forces to the cement;
   wherein no traumatic force is applied to the bone by the vibration and rotation of the tool.

22. The surgical apparatus of claim 21, wherein the opening of the elongated hollow tool at the end applied to the cement to has a reduced diameter portion relative to the rest of said tool.

23. The surgical apparatus of claim 22, wherein the reduced diameter portion of the elongated hollow tool forms a semicircular trough having longitudinally running edges for shearing the cement.

24. The surgical apparatus of claim 21, wherein said rotation means comprises a motor for generating rotational forces and means for transmitting said forces to said vibration source and to said elongated hollow tool for rotation thereof.

25. The surgical apparatus of claim 21, wherein said vibration source includes:
   a tubular piezoelectric crystal having means for electrical contact;
   a union member for connecting said crystal to said elongated hollow tool and having a central passage therethrough, communicating with the elongated hollow tool; and
   a hollow stem disposed inside said crystal, extending opposite from said elongated hollow tool.

26. A surgical apparatus for removing cement from bone or bone cavities, comprising:
   an elongated hollow tool for applying mechanical vibrations to cement present on a bone or bone cavity of a subject to melt the cement by vibration;
   means for removing the melted cement from the bone or bone cavity through the elongated tool by suction or aspiration;
   a handpiece having first and second ends with a first opening defined by the first end and said tool extending from said first opening;
   a vibration source within the handpiece for generating mechanical vibrations in response to electrical current applied thereto, said vibration source operatively associated with the elongated hollow tool to vibrate said tool with said tool being attached to the handpiece at a point where no vibration occurs; and
   means for rotation of said tool operatively associated with said vibration source wherein said means for rotation enables said tool to rotate about its longitudinal axis through at least one revolution while vibrating to apply shearing forces to the cement;
   wherein said vibration source includes:
   a tubular piezoelectric crystal having means for electrical contact;
   a union member for connecting said crystal to said elongated hollow tool and having a central passage therethrough, communicating with the elongated hollow tool; and
   a hollow stem disposed inside said crystal extending opposing from said elongated hollow tool;
   wherein the stem has a length which is not resonant at the operating frequency of the crystal, and the elongated hollow tool means has a length of $\Gamma/4 + n\Gamma/2$ where n is 0 or a positive integer and $\Gamma = f/c$ where f is the frequency of operation and c is the velocity of the extensional waves in said elongated hollow tool.

27. A surgical apparatus for removing cement from bone or bone cavities comprising:
   an elongated hollow tool for applying mechanical vibrations to cement present on a bone or bone cavity of a subject to melt the cement by vibration without applying traumatic force to the bone;
   means for removing the melted cement from the bone or bone cavity unidirectionally through the elongated tool by suction or aspiration;
   a handpiece having first and second ends with a first opening defined by the first end and said tool extending from said first opening;
   a vibration source within the handpiece for generating mechanical vibrations in response to electrical current applied thereto, said vibration source operatively associated with the elongated hollow tool to vibrate said tool with said tool being attached to the handpiece at a point where no vibration occurs; and
   means for cooling and damping lateral vibration at the end of said hollow tool to assist in removal of the melted cement wherein said cooling and damping means is oriented and positioned concentrically about the hollow tool.

28. The surgical apparatus of claim 27, wherein said vibration source includes:
   a tubular piezoelectric crystal having means for electrical contact;
   a union member for connecting said crystal to said elongated hollow tool and having a central passage therethrough, communicating with the elongated hollow tool; and
   a hollow stem disposed inside said crystal, extending opposite from said elongated hollow tool.

29. The surgical apparatus of claim 28, wherein said cooling and clamping means comprises:
   a hollow sleeve having first and second ends surrounding the elongated hollow tool defining an interspace between said tool and said sleeve, said sleeve first end communicating with the first opening in the handpiece, and said hollow tool extending beyond said sleeve second end, wherein a portion of the hollow tool at the end contacting the cement is cut away to define a trough shape at the end, with said cut away beginning inside the second end of the sleeve; and a hollow tube disposed inside said hollow stem defining a second interspace between said tube and said stem, said tube communicating with said central passage for the passage of aspirated material therethrough, and said second interspace communicating with said first interspace through cooling ports defined by the union member for the passage of cooling and damping fluid therethrough.

30. A surgical apparatus for removing cement from bone or bone cavities, comprising:

an elongated hollow tool for applying mechanical vibrations to cement present on a bone or bone cavity of a subject to melt the cement by vibration;

means for removing the melted cement from the bone or bone cavity through the elongated tool by suction or aspiration;

a handpiece having first and second ends with a first opening defined by the first end and said tool extending from said first opening;

a vibration source within the handpiece for generating mechanical vibrations in response to electrical current applied thereto, said vibration source operatively associated with the elongated hollow tool to vibrate said tool with said tool being attached to the handpiece at a point where no vibration occurs; and means for cooling and damping lateral vibration at the end of said hollow tool to assist in removal of the melted cement;

wherein said cooling and damping means is oriented and positioned concentrically about the hollow tool;

wherein said vibration source includes:

a tubular piezoelectric crystal having means for electrical contact;

a union member for connecting said crystal to said elongated hollow tool and having a central passage therethrough, communicating with the elongated hollow tool; and a hollow stem disposed inside said crystal extending opposing from said elongated hollow tool; and wherein said cooling and damping means comprises:

a hollow sleeve having first and second ends surrounding the elongated hollow tool defining an interspace between said tool and said sleeve, said sleeve first end communicating with the first opening in the handpiece, and said hollow tool extending beyond said sleeve second end, wherein a portion of the hollow tool at the end contacting the cement is cut away to define a trough shape at the end, with said cut away beginning inside the second end of the sleeve; and a hollow tube disposed inside said hollow stem defining a second interspace between said tube and said stem, said tube communicating with said central passage for the passage of aspirated material therethrough, and said second interspace communicating with said first interspace through cooling ports defined by the union member for the passage of cooling and damping fluid therethrough;

wherein the stem has length which is not resonant at the operating frequency of the crystal, and the elongated hollow tool means has a length or $\Gamma/4 + n\Gamma/2$ wherein n is 0 or a positive integer and $\Gamma = f/c$ where f is the frequency of operation and c is the velocity of extensional waves in said elongated hollow tool.

31. A surgical apparatus for removing cement from bone or bone cavities comprising:

a handpiece;

a vibration source within the handpiece for generating mechanical vibrations in response to electrical current applied thereto, said vibration source including a tubular piezoelectric crystal, a union member having a central passage therethrough, and a hollow stem disposed inside said crystal;

an elongated hollow tool connected to the vibration source at the union member and vibrated thereby, said tool attached to said handpiece at a point where essentially no vibration occurs, said hollow tool including an inner tubular member communicating with the central passage of the union member at one end and extending beyond an outer tubular at the opposite end for apply vibration to bone cement without applying traumatic force to the bone, said outer tubular member defining an interspace between said tubular members, and said interspace communicating with cooling ports defined by the union member; and means for aspiration of the cement, cooling the hollow tool and damping lateral vibrations in the hollow tool, said means including a hollow tube disposed inside said hollow stem defining a second interspace between said tube and said stem, said tube communicating with said central passage for the unidirectional passage of aspirated cement material therethrough, and said second interspace communicating with said first interspace through said cooling ports for the passage of cooling and damping fluid therethrough, and wherein a portion of the inner tubular member is cut away to form a trough the end extending beyond the outer tubular member, said trough extending from the end of the inner tubular member to inside the outer tubular member.

32. The apparatus of claim 31 wherein the elongated tool means is vibrated and rotated simultaneously.

33. A method of removing cement from bone or bone cavities containing same which comprises:

applying mechanical vibrations to cement present on a bone or bone cavity of a subject to melt an area of the cement by vibration; and removing the melted cement from the bone or bone cavity by suction or aspiration wherein no traumatic force is applied to the bone, wherein the cement is removed without interruption.

* * * * *